United States Patent [19]

Sano et al.

[11] Patent Number: 5,701,903
[45] Date of Patent: Dec. 30, 1997

[54] FLUOROSCOPIC APPARATUS

[75] Inventors: Hiroshi Sano; Rensuke Adachi, both of Tokyo, Japan

[73] Assignee: Asahi Kogaku Kogyo Kabushiki Kaisha, Tokyo, Japan

[21] Appl. No.: 493,680

[22] Filed: Jun. 22, 1995

[30] Foreign Application Priority Data

Jun. 23, 1994 [JP] Japan .................. 6-141474

[51] Int. Cl.$^6$ .................................................. A61B 1/00
[52] U.S. Cl. ................... 128/665; 600/109; 600/160; 348/49; 348/68; 128/664
[58] Field of Search .......................... 128/665, 664, 128/634; 600/109, 112, 153, 160, 168, 172, 178, 181; 348/45, 47, 49, 54, 65, 68, 72–76

[56] References Cited

U.S. PATENT DOCUMENTS

| 4,821,117 | 4/1989 | Sekiguchi . |
|---|---|---|
| 4,895,138 | 1/1990 | Yabe . |
| 4,993,404 | 2/1991 | Lane . |
| 5,051,824 | 9/1991 | Nishigaki . |
| 5,078,150 | 1/1992 | Hara et al. . |
| 5,241,170 | 8/1993 | Field, Jr. et al. . |
| 5,318,024 | 6/1994 | Kittrell et al. . |
| 5,394,499 | 2/1995 | Ono et al. . |
| 5,408,996 | 4/1995 | Salb . |
| 5,605,531 | 2/1997 | Lane et al. . |
| 5,608,451 | 3/1997 | Konno et al. . |
| 5,608,520 | 3/1997 | Fleming . |

OTHER PUBLICATIONS

Japanese Unexamined Patent Publication No. 1-221137.
Japanese Unexamined Patent Publication No. 2-299634.
Japanese Unexamined Patent Publication No. 4-150845 (This is the English equivalent of U.S. Ser. No. 07/770,332— now abandoned).

*Primary Examiner*—Marvin M. Lateef
*Assistant Examiner*—Shawna J. Shaw
*Attorney, Agent, or Firm*—Kane,Dalsimer,Sullivan,Kurucz, Levy, Eisele and Richard, LLP

[57] ABSTRACT

A fluoroscopic apparatus in which an object image formed by an objective optical system provided at a front end of an insertion portion of an endoscope is transmitted to an ocular optical system through a first bundle of image guiding optical fibers to view the object image includes an excitation light filter which permits light having a wavelength band for exciting fluorescence from an object to be viewed to pass therethrough. The excitation light filter is retractably inserted in an optical path of illuminating light with which the object is illuminated. A beam splitter is provided in the ocular optical system to split the object image transmitted to the ocular optical system into an image for normal observation and for an image for fluorescence observation. A second bundle of image guiding optical fibers is provided in an optical path of the image for fluorescence observation to transmit the image to an image intensifier. Another filter for fluorescence observation is provided in the optical path of the image to permit light having a wavelength band other than the wavelength band which can pass through the excitation light filter to pass therethrough.

6 Claims, 4 Drawing Sheets

FLUOROSCOPIC APPARATUS

BACKGROUND OF THE INVENTION

1. Field of the Invention

The present invention relates to a fluoroscopic apparatus which is used to diagnose, for example, an early cancer through fluorescence observation using an endoscope.

2. Description of Related Art

In an endoscope used in an endoscope apparatus for a fluorescence diagnosis, an object image obtained through an objective optical system provided at a front end of an insertion portion of the endoscope is transmitted to an ocular optical system through a bundle of optical fibers inserted in the insertion portion, similarly to a conventional endoscope apparatus as a viewing optical instrument.

For normal observation, a standard TV camera is attached to the ocular optical system. Upon fluorescence observation, the standard TV camera is replaced with a TV camera having an image intensifier. The TV camera having the image intensifier is so heavy that an operator cannot easily or conveniently operate the endoscope when performing fluorescence observation. Moreover, it is necessary to replace the standard TV camera with the TV camera having the image intensifier and vice versa, every time normal observation or the fluorescence observation is switched according to which observation is to be performed.

SUMMARY OF THE INVENTION

It is an object of the present invention to provide a fluoroscopic apparatus in which the operation is simplified and the switching between normal observation and fluorescence observation can be easily effected.

To achieve the object mentioned above, according to the present invention, there is provided a fluoroscopic apparatus in which an object image formed by an objective optical system provided at a front end of an insertion portion of an endoscope is transmitted to an ocular portion through a first bundle of image guiding optical fibers to view the object image, comprising an excitation light filter which permits light having a wavelength band for exciting fluorescence from an object to be viewed to pass therethrough, the excitation light filter being retractably inserted in an optical path of illuminating light with which the object is illuminated; a beam splitter provided in the ocular portion to split the object image transmitted to the ocular portion into an image for normal observation and an image for fluorescence observation; a second bundle of image guiding optical fibers provided in an optical path of the image for fluorescence observation to transmit the image to an image intensifier; and, a filter for fluorescence observation, provided in the optical path of the image for fluorescence observation to permit light having a wavelength band other than the wavelength band which can pass through the excitation light filter to pass therethrough.

Preferably at least the beam splitter and the second bundle of image guiding optical fibers are detachably attached to the ocular portion. The images for normal observation and fluorescence observation split by the beam splitter can be shown on a same monitor. The images for normal observation and the fluorescence observation, shown on the same monitor preferably have substantially a same size.

According to another aspect of the present invention, there is provided a fluoroscopic apparatus comprising: an endoscope having an objective optical system and ocular optical system to view an object image; a light source for illuminating the object; a first filtering means which permits light having a wavelength band for exciting fluorescence from an object to be viewed to pass therethrough from light emitted from the light source; means for moving the first filtering means between an inserted position in front of the light source and a retracted position from the light source; a beam splitter provided in the ocular optical system to split the object image transmitted to the ocular optical system into a normal observation optical path and a fluorescence observation optical path; means for normal observation provided in the normal observation optical path; and means for fluorescence observation provided in the fluorescence observation optical path, the fluorescence observation means comprising a second filtering means which permits light having a wavelength band other than the wavelength band which can pass through the first filtering means to pass therethrough.

The present disclosure relates to subject matter contained in Japanese patent application No. 06-141474 (filed on Jun. 23, 1994) which is expressly incorporated herein by reference in its entirety.

BRIEF DESCRIPTION OF THE DRAWINGS

The invention will be described below in detail with reference to the accompanying drawings, in which.

DESCRIPTION OF THE PREFERRED EMBODIMENT

Figure 1:
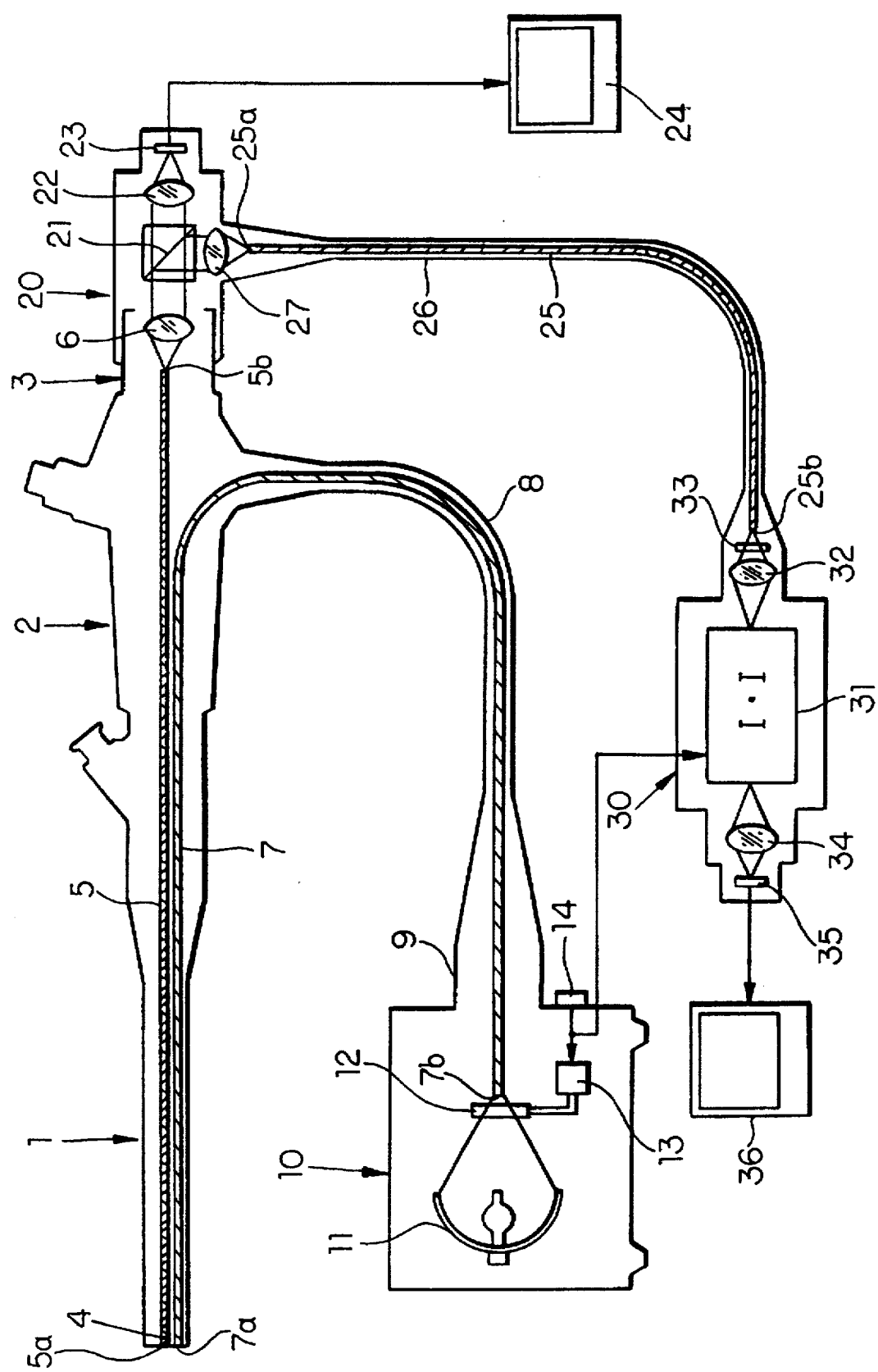
FIG. 1 is a schematic view of a fluoroscopic apparatus according to a first embodiment of the present invention.

FIG. 1 shows a first embodiment of a fluoroscopic apparatus according to the present invention. An endoscope has an insertion portion 1, an operating portion 2 connected to the base end of the insertion portion 1, and an ocular portion 3 projecting from the operating portion 2. An objective optical system 4 is incorporated in the front end of the insertion portion 1 to converge and form an object image onto an incident surface 5a of a bundle of image guiding optical fibers 5. The optical fibers 5 extend in the operating portion 2 so that the emitting end 5b of the optical fibers 5 reaches the ocular portion 3. The ocular portion 3 includes an ocular optical system 6 incorporated therein, through which an enlarged size of the emitting end 5b of the optical fibers 5 can be viewed. Consequently, an image of an object which is located in front of the insertion portion 1 is formed by the objective optical system 4 and transmitted to the ocular portion 3 through the optical fibers 5, so that an operator can view the object image through the ocular optical system 6.

A bundle of optical fibers 7, through which illuminating light is transmitted so as to illuminate the object, extends from the emitting end 7a thereof in parallel with the objective optical system 4 and passes through the insertion portion 1, the operating portion 2 and a light guiding connecting tube 8. The incident end 7b of the optical fibers 7 is disposed in a connector 9 which is detachably attached to a light source 10.

The light source 10 includes a xenon lamp 11 which emits illuminating light which is converged to be made incident upon the incident end 7b of the optical fibers 7. Therefor, illuminating the object emitted from the emitting end 7a of the optical fibers 7.

A band-pass filter 12 for exciting light excitation is retractably inserted between the incident end 7b of the optical fibers 7 and the xenon lamp 11 to permit only light having a wavelength band ranging from about 420–480 nm to pass therethrough. The band-pass filter 12 is inserted in and retracted from the optical path of the illuminating light to be received by the optical fibers 7 by a solenoid 13 which is actuated in response to the operation of a selection switch 14. When the light whose wavelength band ranges from 420 nm to 480 nm is made incident upon a normal tissue of a living body, the normal tissue will emit light having a wavelength band ranging from 520 nm to 600 nm.

In the illustrated embodiment, the solenoid 13 is inactivated, so that the band-pass filter 12 is retracted from the optical path of the illuminating light, upon normal observation. Upon fluorescence observation, the solenoid 13 is activated to move the band-pass filter 12 into the optical path of the illuminating light.

Figure 2:
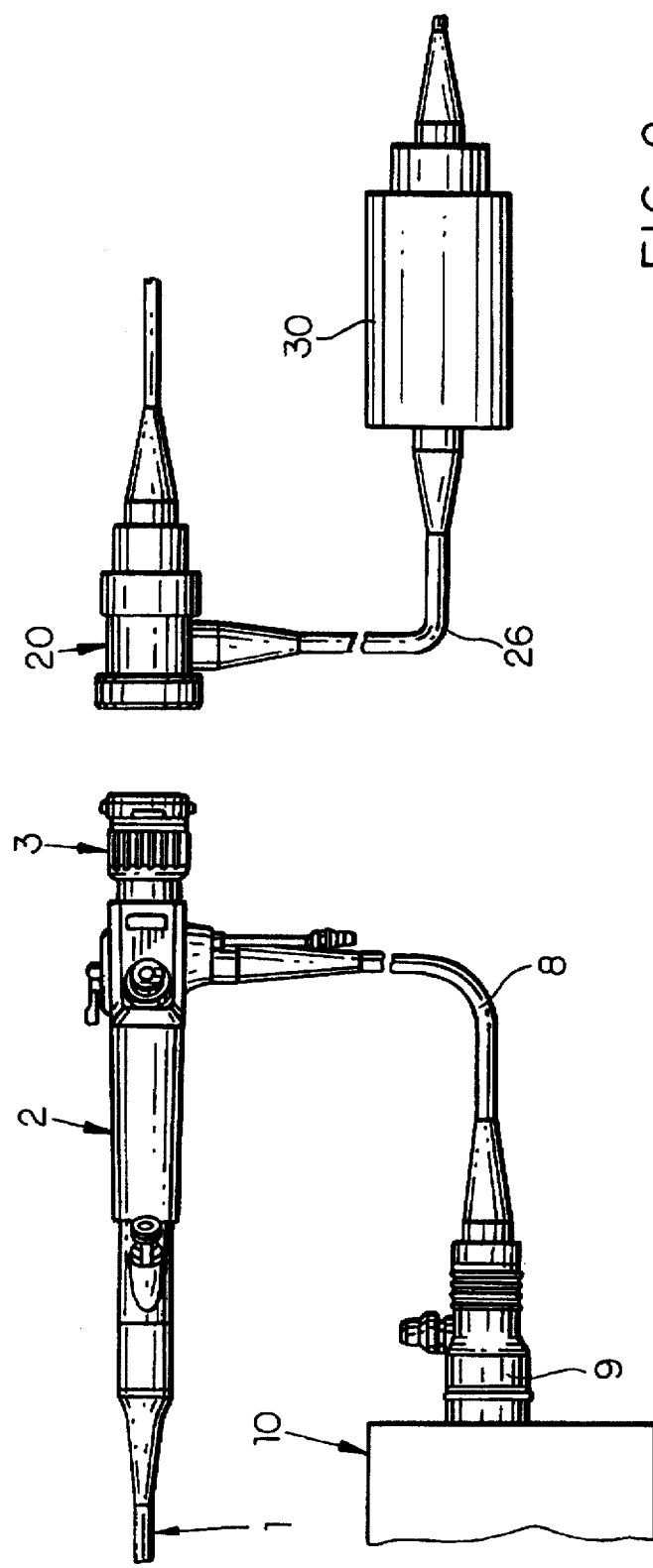
FIG. 2 is a front elevation view of a fluoroscopic apparatus having a disconnected insertion portion.

An eyepiece adapter 20 is detachably connected to the ocular portion 3. The eyepiece adapter 20 is connected to and disconnected from the ocular portion 3 as shown in FIG. 1 and FIG. 2, respectively. The connecting mechanism of the eyepiece adapter 20 and the ocular portion 3 is commonly used for an eyepiece attachment/detachment of a conventional endoscope. For example, a bayonet connector can be used.

A beam splitter 21 is provided in the eyepiece adapter 20 to split the optical path of the object image transmitted through the bundle of optical fibers 5 and the ocular optical system 6 into an optical path for normal observation and optical path for fluoroscence observation. The beam splitter 21 is made of, for example, two right-angle prisms which are cemented at their oblique connecting surfaces which are provided with a semitransparent film as shown in FIG. 1, or a thin half mirror, etc.

Within the eyepiece adapter 20, an image forming lens 22, which converges and forms an object image transmitted through the beam splitter 21 and a solid state image pickup device 23 for normal observation, which is located at an image forming position to receive the object image to thereby convert the object image to electric signals are provided. The object image for normal observation, formed by visible light of all wavelengths is shown on the TV monitor 24 for normal observation, in accordance with the image signals (electric signals) output from the solid state image pickup device 23 for normal observation.

Alternatively, it is possible for an operator (viewer) to directly observe the object image transmitted through the beam splitter 21 and enlarged by a magnifying lens or the like, provided in place of the image forming lens 22. In this alternative it is unnecessary to provide the solid state image pickup device 23 and the TV monitor 24 for normal observation.

A flexible image guiding and connecting tube 26, provided with a second bundle of image guiding optical fibers 25, is connected to a side surface of the eyepiece adapter 20. Consequently, the object image reflected toward the lateral direction by the beam splitter 21 is formed on the incident surface 25a of the second bundle of the optical fibers 25 through a second image forming lens 27 provided in the eyepiece adapter 20. The object image incident upon the second bundle of optical fibers 25 is transmitted to the emitting end 25b thereof.

The connecting tube 26 is attached at the other end to an amplifying TV camera 30 having an image intensifier 31 incorporated therein so as to remarkably increase the intensity of light, so that the object image formed on the emitting end 25b of the second bundle of optical fibers 25 can be projected onto the image intensifier 31 by the image forming lens 32.

A band-pass filter 33 for fluoroscence observation is provided between the emitting end 25b of the second bundle of optical fibers 25 and the image forming lens 32 to permit only light having a wavelength band ranging from about 520 nm to 600 nm to pass therethrough. Consequently, only light having a wavelength ranging from 520 nm to 600 nm is made incident upon the image intensifier 31.

When an organic tissue receives light having a wavelength band ranging from about 420 nm to 480 nm transmitted through the band-pass filter 12 for the excitation light, normal tissue non-cancerous tissue emits a fluoroscence ranging from about 520–600 nm, but cancerous tissue emits no fluoroscence. Consequently, when the band-pass filter 12 is inserted in the optical path of the illuminating light, the fluoroscence emitted from the normal tissue is received and intensified by the image intensifier 31.

When the band-pass filter 12 is retracted from the optical path of the illuminating light, the intensity of light incident upon the image intensifier 31 is too concentrated. To prevent this, the selection switch 14 also serves as a power switch for the image intensifier 31. Specifically, when the band-pass filter 12 is retracted from the optical path, the power switch 14 of the image intensifier 31 is automatically turned OFF, and only when the band-pass filter 12 is inserted in the optical path, the power switch 14 of the image intensifier 31 is turned ON.

The object image for fluoroscence observation, intensified by the image intensifier 31 is formed by the image forming lens 34 on the solid state image pickup device 35 for fluoroscence observation. Subsequently, the image is shown on the TV monitor 36 for fluoroscence observation in accordance with the image signals output from the solid state image pickup device 35.

In the fluoroscope as constructed above, for a patient who is not to be subjected to fluoroscence observation, the eyepiece adapter 20 is detached from the ocular portion 3, and observation is carried out by the insertion portion 1 having no eyepiece adapter connected thereto. On the other hand, for a patient who is to be subjected to fluoroscence observation, the eyepiece adapter 20 is attached to the ocular portion 3.

The selection switch 14 is maintained in the OFF state to retract the band-pass filter 12 for excitation light from the optical path of illuminating light until commencement of fluoroscence observation. In this state, the power switch of the image intensifier 31 is turned OFF, and the object image for normal observation is shown on the TV monitor 24 for the normal observation.

Upon fluoroscence observation, the selection switch 14 is turned ON, so that the band-pass filter 12 is inserted in the optical path of the illuminating light, thereby causing the power switch of the image intensifier 31 to be turned ON. As a result, the object image for the fluoroscence observation is shown on the TV monitor 36.

In this state, a blue image of an object illuminated with the illuminating light having a wavelength band ranging from about 420–480 nm is shown on the TV monitor 24 for the normal observation. A specific portion to be viewed can accurately identified by the blue object image. Although the fluorescence having a wavelength band of about ranging from 520–600 run is also shown on the TV monitor 24 for the normal observation, but its intensity is too weak thereby making it impossible to view.

As can be understood from the above discussion, upon fluoroscence observation, not only it is not unnecessary to connect the TV camera to the ocular portion during examination, but also no heavy image intensifier 31 is connected to the ocular portion 3, and hence, an operator can easily handle the endoscope while holding the operating portion 2.

Figure 3:
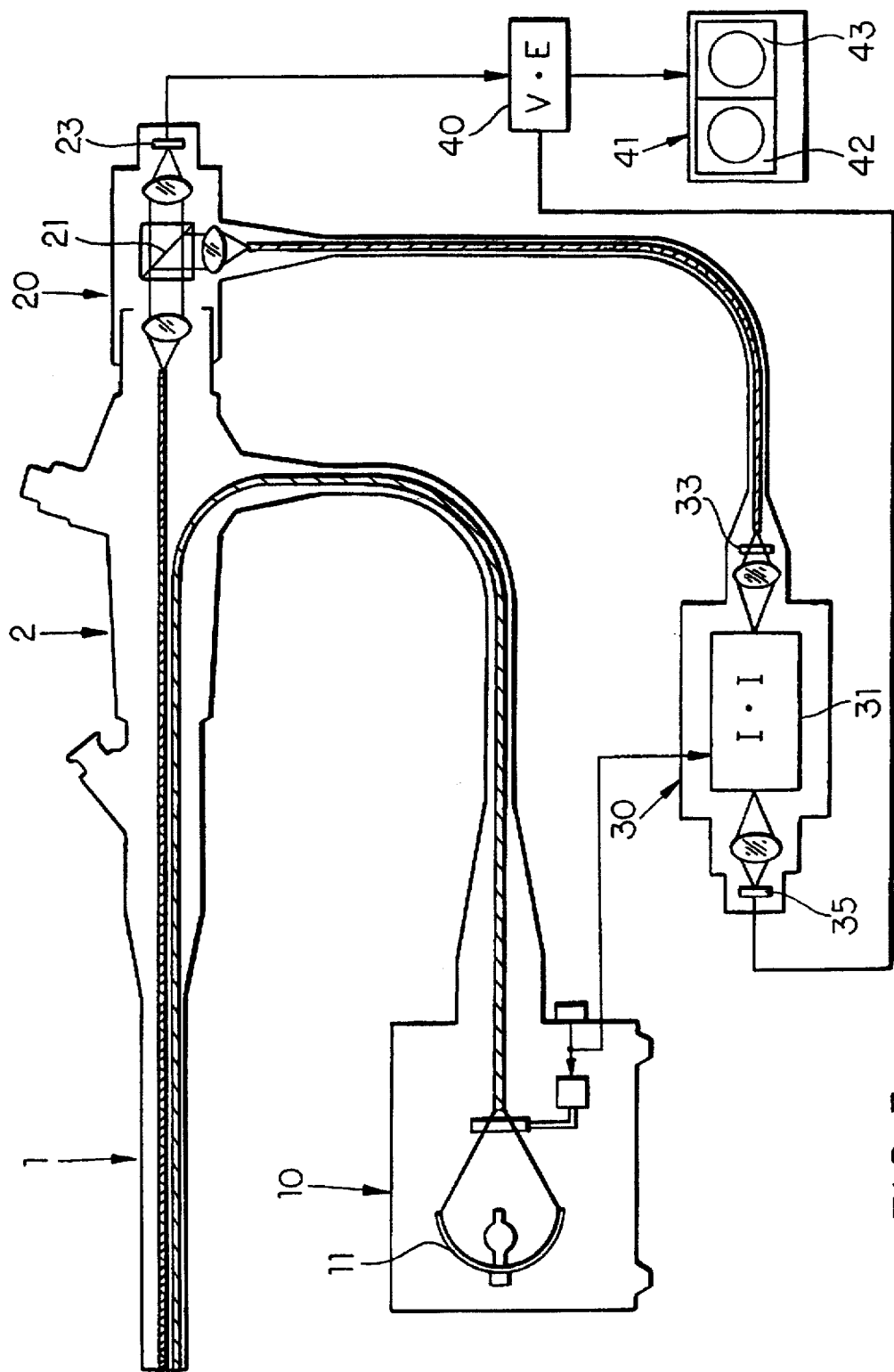
FIG. 3 is a schematic view of a fluoroscopic apparatus according to a second embodiment of the present invention.

FIG. 3 shows a second embodiment of a fluoroscopic apparatus according to the present invention. In the second embodiment, the image signals supplied from the solid state image pickup device 23 of the eyepiece adapter 20 for normal observation and the image signals supplied from the solid state image pickup device 35 of the amplifying TV camera 30 for fluoroscence observation are input to a video editor 40 so that both the images are shown side-by-side on the same TV monitor 41. The structure of the second embodiment is the same as that of the first embodiment except for the above-mentioned features.

With this arrangement, the body portion (tissue) to be observed can be easily identified. It is preferred that the object image 42 for normal observation supplied from the solid state image pickup device 23 and the object image 43 for fluoroscence observation supplied from the solid state image pickup device 35 are the same size as viewed on the TV monitor 41, so that the body portion for fluoroscence observation can be more easily identified.

Figure 4:
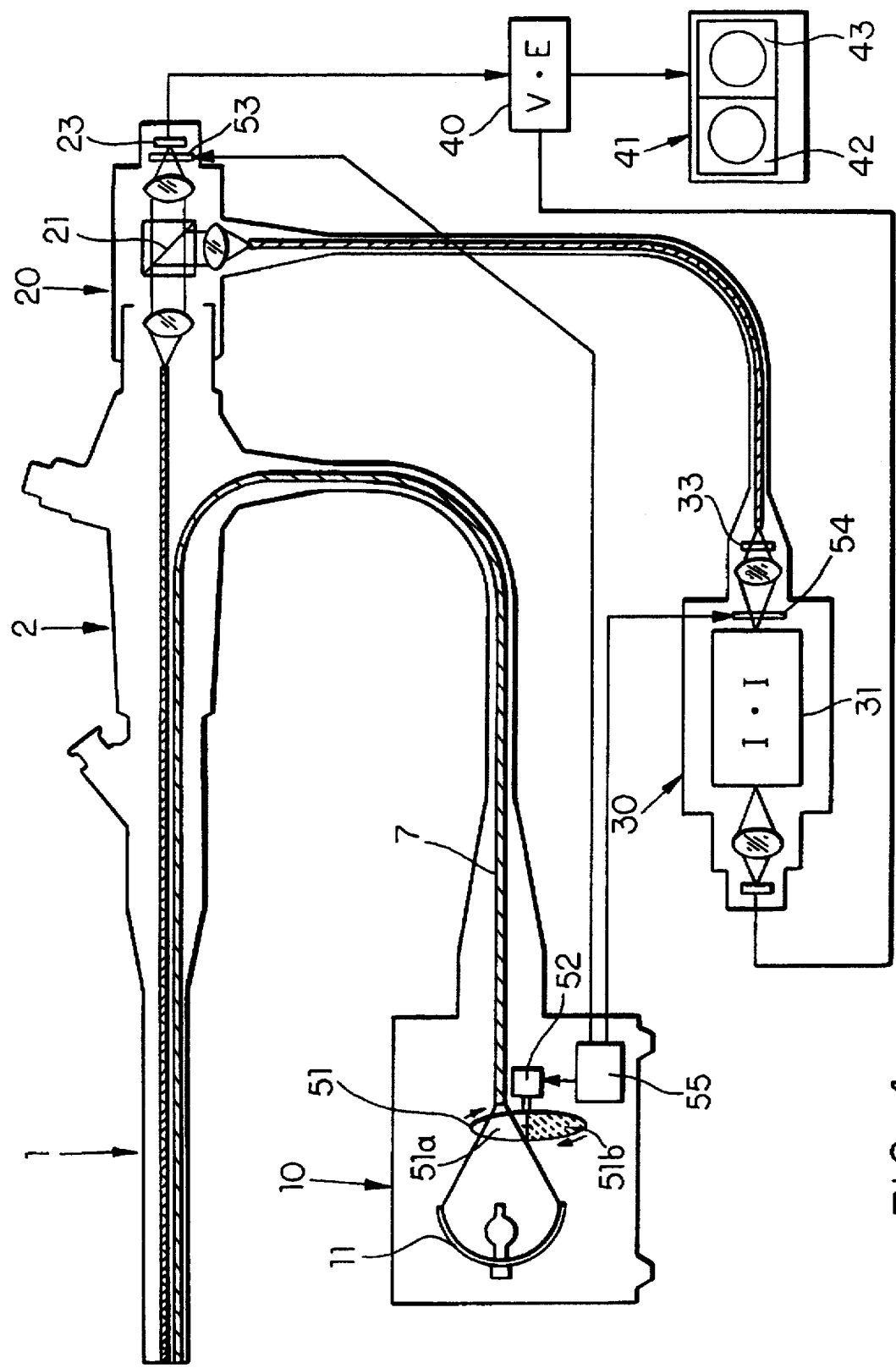
FIG. 4 is a schematic view of a fluoroscopic apparatus according to a third embodiment of the present invention; and, FIG. 5 is a front elevational view of a rotatable filter in a third embodiment shown in FIG. 4.

FIG. 4 shows a third embodiment of a fluoroscopic apparatus according to the present invention.

Figure 5:
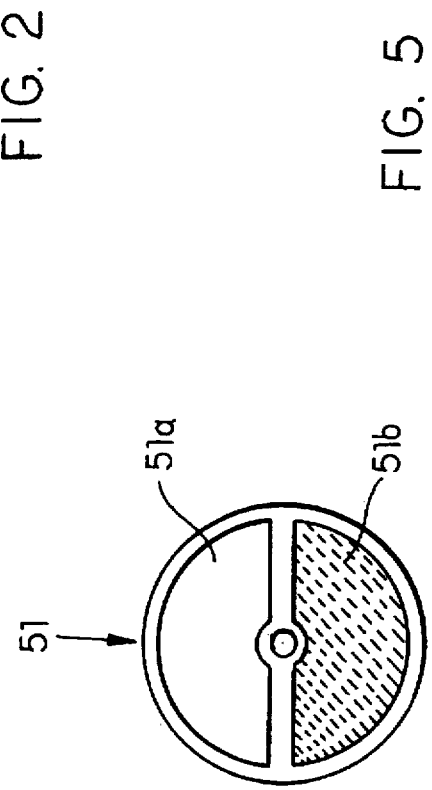

In the third embodiment, a rotatable filter 51 is provided between the xenon lamp 11 of the light source 10 and the incident end of the bundle of optical fibers 7. The rotatable filter 51 is provided with a transparent portion 51a through which all wavelengths can be transmitted and a filter portion 51b which permits only light ranging from about 420 nm to 480 nm to pass therethrough, as can be seen in FIG. 5. The rotatable filter 51 which has a circular shape is rotated at a constant speed by a motor 52 (FIG. 4) about the center axis.

A first shutter 53 for normal observation is provided in front of the light receiving surface of the solid state image pickup device 23 of the eyepiece adapter 20 to selectively interrupt the light, for normal observation, to be made incident upon the solid state image pickup device 23. A second shutter 54 for fluoroscence observation is provided in front of the light receiving surface of the image intensifier 31 of the light intensifying camera 30 to selectively interrupt the light, for fluorescence observation, to be made incident upon the image intensifier 31.

The rotation of the rotatable filter 51 and the opening and closing of the first and second shutters 53 and 54 are synchronously controlled by a synchronization control circuit 55 provided in the light source 10, so that the object image for fluorescence observation and the object image of all wavelengths for normal observation are alternately conveyed to the video editor 40, so that both object images are simultaneously shown on the TV monitor 41. The structure of the third embodiment is the same as that of the second embodiment except for the above-mentioned features.

The present invention is not limited to the illustrated embodiments. For instance, the wavelength band which can pass through the band-pass filter 33 for the fluorescence observation is not precisely limited to 520–600 nm. Specifically, the band-pass filter 33 permits light having a wavelength band other than the wavelength band which can pass through the band-pass filter 12 for the excitation light and including the wavelength of the excited fluorescence. Moreover, the band-pass filter 33 for fluorescence observation can be provided on the incident side of the second bundle of optical fibers 25.

As can be understood from the above discussion, according to the present invention, since both normal observation and fluorescence observation can be effected without connecting a TV camera to the ocular portion during endoscopic examination, no troublesome operation is required to connect or disconnect the TV camera. Moreover, since no heavy image intensifier is connected to the ocular portion, an operator can easily operate the endoscope while holding the operating portion.

In addition to the foregoing, if the beam splitter and the second bundle of optical fibers, etc., are detachably attached to the ocular portion, these detachable elements can be removed when no fluorescence observation is necessary thereby reducing the overall weight of the entire apparatus.

In this case where the object images for normal observation and fluorescence observation, split by the beam splitter are shown on the same monitor, the body portion to be subjected to fluorescence observation can be easily identified. In addition, if the object images for normal observation and fluorescence observation, shown on the monitoring display are substantially identical in size, the body portion to be subjected to fluorescence observation can be more easily identified.

We claim:

1. A fluoroscopic apparatus in which an object image formed by an objective optical system provided at a front end of an insertion portion of an endoscope is transmitted to an ocular portion through a first bundle of image guiding optical fibers to view the object image, comprising;

an excitation light filter which permits light having a wavelength band for exciting fluorescence from an object to be viewed to pass therethrough, said excitation light filter being retractably inserted in an optical path of illuminating light with which the object is illuminated;

a beam splitter provided in the ocular portion to split the object image transmitted to the ocular portion through said first bundle of image guiding optical fibers into an image for normal observation and an image for fluorescence observation;

a first image pickup device provided for receiving said image for normal observation, said first image pickup device being positioned behind said beam splitter in an optical path for normal observation extending from said beam splitter;

a first image forming lens in said optical path for normal observation disposed between said beam splitter and said first image pickup device, said first image forming lens converging and forming an object image of light transmitted through said beam splitter;

an optical path of the image for fluorescence observation extending from said beam splitter to a second image pickup device;

an image intensifier disposed outside said ocular portion and within said optical path for florescence observation;

a second bundle of image guiding optical fibers provided in said optical path of the image for fluorescence observation to transmit the image from said beam splitter to said image intensifier;

a second image forming lens in said optical path for fluorescence observation disposed between said beam splitter and said image intensifier, said second image forming lens converging and forming an object image of light transmitted through said beam splitter onto a receiving surface of said second bundle of image guiding optical fibers;

a filter for fluorescence observation, provided in the optical path of the image for fluorescence observation to permit light having a wavelength band other than the wavelength band which can pass through the excitation light filter to pass therethrough; and a second image pickup device positioned in said optical path for fluorescence observation behind said image intensifier to receive an image intensified by said image intensifier.

2. A fluoroscopic apparatus according to claim 1, wherein at least said beam splitter and said second bundle of image guiding optical fibers are detachably attached to the ocular optical system.

3. A fluoroscopic apparatus according to claim 1, wherein the images for normal observation and fluorescence observation split by the beam splitter are shown on a same monitor.

4. A fluoroscopic apparatus according to claim 3, wherein the images for normal observation and fluorescence observation, shown on the same monitor have substantially a same size.

5. A fluoroscopic apparatus according to claim 1, wherein said excitation light filter comprises a rotatable filter having a transparent portion which permits light of all wavelengths to pass therethrough and a filter portion which permits light having a wavelength band for exciting fluorescence from an object to be viewed to pass therethrough.

6. A fluoroscopic apparatus according to claim 5, further comprising a first shutter provided in the normal observation optical path, a second shutter provided in the fluorescences optical path, and control means for opening and closing the first and second shutters in synchronization with the rotation of the rotating filter.

* * * * *